(12) United States Patent
Jones et al.

(10) Patent No.: US 9,295,855 B2
(45) Date of Patent: Mar. 29, 2016

(54) AMBIENT SPECTRUM LIGHT CONVERSION DEVICE

(71) Applicants: Gary W. Jones, Newcastle, WA (US); Susan K. Schwartz Jones, Newcastle, WA (US)

(72) Inventors: Gary W. Jones, Newcastle, WA (US); Susan K. Schwartz Jones, Newcastle, WA (US)

(*) Notice: Subject to any disclaimer, the term of this patent is extended or adjusted under 35 U.S.C. 154(b) by 0 days.

(21) Appl. No.: 14/217,418

(22) Filed: Mar. 17, 2014

(65) Prior Publication Data
US 2014/0277294 A1    Sep. 18, 2014

Related U.S. Application Data

(60) Provisional application No. 61/801,602, filed on Mar. 15, 2013.

(51) Int. Cl.
*F21V 9/16* (2006.01)
*A61N 5/06* (2006.01)

(52) U.S. Cl.
CPC ............ *A61N 5/062* (2013.01); *A61N 5/0616* (2013.01); *A61N 5/0618* (2013.01);
(Continued)

(58) Field of Classification Search
CPC .. A61F 9/022; A61N 5/06; A61N 2005/0662; A61N 2005/0665; A61N 2005/0667; A61N 5/062; A61N 2005/0657; A61N 2005/0628; A61N 5/0616; A61N 5/0618; G02F 2001/133614
See application file for complete search history.

(56) References Cited

U.S. PATENT DOCUMENTS

| 4,646,743 A | 3/1987 | Parris |
| 5,800,478 A | 9/1998 | Chen et al. |

(Continued)

FOREIGN PATENT DOCUMENTS

| CN | 202871750 U | 4/2013 |
| WO | 2008041138 A2 | 4/2008 |

(Continued)

OTHER PUBLICATIONS

Allan, M., "Opportunities in Cancer Therapeutics: Roswell Park Cancer Institute Photodynamic Therapy Patent Portfolio", 2009, pp. 1-4, Publisher: First Principals, Inc., Published in: Cleveland, OH.

(Continued)

*Primary Examiner* — Gary Jackson
*Assistant Examiner* — Scott T Luan
(74) *Attorney, Agent, or Firm* — Hultquist IP; Steven J. Hultquist (57) ABSTRACT

Apparatus and methods to enhance light intensity within useful red to near-infrared spectral ranges, using direct or indirect sunlight, or from other ambient white light, are described. The disclosed devices provide high quantum yield photoluminescent ambient light spectrum conversion to increase the supplied energy primarily in the 590 nm-850 nm spectral range. These devices also pass much of the incident light in the spectral range in which the device's photoluminescent materials emit light, thereby greatly increasing the effective intensity of light available in the targeted 590-850 nm wavelength range. The ambient light conversion devices of the disclosure may be incorporated in apparel, bandage-like patches, converting reflectors, large area converters, awnings, window covers, and other articles, materials, and products. The converted light may be used in therapeutic treatments, horticultural and biotechnological applications, and other applications in which the converted light outputs of the present disclosure are beneficial.

19 Claims, 4 Drawing Sheets (52) U.S. Cl.
CPC ............ *A61N 2005/0628* (2013.01); *A61N 2005/0657* (2013.01); *A61N 2005/0662* (2013.01); *A61N 2005/0665* (2013.01); *A61N 2005/0667* (2013.01)

(56) References Cited

U.S. PATENT DOCUMENTS

| | | | |
|---|---|---|---|
| 5,997,569 | A | 12/1999 | Chen et al. |
| 5,998,925 | A | 12/1999 | Shimizu et al. |
| 6,063,108 | A | 5/2000 | Salansky et al. |
| 6,096,066 | A | 8/2000 | Chen et al. |
| 6,290,713 | B1 | 9/2001 | Russell |
| 6,295,106 | B1 * | 9/2001 | Fukuzawa et al. ............ 349/71 |
| 7,290,896 | B2 | 11/2007 | Dallas et al. |
| 7,304,201 | B2 | 12/2007 | Holloway et al. |
| 7,517,307 | B2 | 4/2009 | Pokusa et al. |
| 7,646,032 | B2 | 1/2010 | Radkov et al. |
| D623,308 | S | 9/2010 | Kramer |
| 8,113,681 | B2 | 2/2012 | Dallas et al. |
| 2004/0105264 | A1 | 6/2004 | Spero |
| 2004/0127961 | A1 | 7/2004 | Whitehurst |
| 2004/0179283 | A1 | 9/2004 | Jones et al. |
| 2005/0131279 | A1 | 6/2005 | Boulais et al. |
| 2005/0182460 | A1 | 8/2005 | Kent et al. |
| 2005/0278003 | A1 | 12/2005 | Feldman |
| 2006/0030908 | A1 | 2/2006 | Powell et al. |
| 2006/0111761 | A1 | 5/2006 | Butler et al. |
| 2006/0197437 | A1 | 9/2006 | Krummacher et al. |
| 2006/0247741 | A1 | 11/2006 | Hsu et al. |
| 2006/0287696 | A1 | 12/2006 | Wright et al. |
| 2007/0167999 | A1 | 7/2007 | Breden et al. |
| 2008/0119913 | A1 | 5/2008 | Powell et al. |
| 2008/0140164 | A1 | 6/2008 | Oberreiter et al. |
| 2008/0172113 | A1 | 7/2008 | Gourgouliatos et al. |
| 2009/0204186 | A1 * | 8/2009 | Gruber ............................ 607/88 |
| 2009/0234340 | A1 | 9/2009 | Behrakis |
| 2009/0234341 | A1 | 9/2009 | Roth |
| 2009/0234342 | A1 | 9/2009 | Ely et al. |
| 2009/0234343 | A1 | 9/2009 | Behrakis |
| 2010/0087898 | A1 | 4/2010 | Clement et al. |
| 2010/0165599 | A1 | 7/2010 | Allen |
| 2010/0179469 | A1 * | 7/2010 | Hammond et al. ............. 604/20 |
| 2010/0289044 | A1 | 11/2010 | Krames et al. |
| 2011/0004201 | A1 | 1/2011 | Nuijs et al. |
| 2011/0182072 | A1 | 7/2011 | Shimizu et al. |
| 2011/0228515 | A1 | 9/2011 | Grajcar |
| 2012/0008217 | A1 | 1/2012 | Ishak et al. |
| 2012/0080615 | A1 | 4/2012 | Kingsley et al. |
| 2012/0255609 | A1 | 10/2012 | Sobue et al. |
| 2012/0293978 | A1 | 11/2012 | Guo et al. |
| 2013/0094036 | A1 | 4/2013 | Itagaki |
| 2013/0134885 | A1 | 5/2013 | Linden et al. |
| 2013/0194794 | A1 | 8/2013 | Kim |
| 2013/0255778 | A1 | 10/2013 | Okaniwa et al. |
| 2013/0296976 | A1 * | 11/2013 | Maxik et al. .................... 607/88 |
| 2013/0344454 | A1 | 12/2013 | Nath |

FOREIGN PATENT DOCUMENTS

| | | |
|---|---|---|
| WO | 2011048458 A1 | 4/2011 |
| WO | 2011120172 A1 | 10/2011 |
| WO | 2011132125 A1 | 10/2011 |
| WO | 2012025399 A1 | 3/2012 |
| WO | 2012042415 A1 | 4/2012 |
| WO | 2012134992 A2 | 10/2012 |
| WO | 2012168395 A1 | 12/2012 |

OTHER PUBLICATIONS

Uvbiotek LLC, "Phototherapy systems designed to fit the way you live", 2006, pp. 1-6, Published in: North Fort Myers, FL.
Unpublished U.S. Appl. No. 14/217,356, filed Mar. 17, 2014.
Unpublished U.S. Appl. No. 14/262,794, filed Apr. 27, 2014.

\* cited by examiner

AMBIENT SPECTRUM LIGHT CONVERSION DEVICE

CROSS REFERENCE TO RELATED APPLICATION

The benefit of U.S. Provisional Patent Application No. 61/801,602 filed Mar. 15, 2014 in the names of Gary W. Jones and Susan K. Schwartz Jones for "AMBIENT SPECTRUM LIGHT CONVERSION DEVICE" is hereby claimed under the provisions of 35 USC 119. The disclosure of U.S. Provisional Patent Application No. 61/801,602 is hereby incorporated herein by reference in its entirety, for all purposes.

FIELD

The present disclosure relates generally to apparatus and methods to enhance light intensity within therapeutic or otherwise biologically useful red to near-infrared spectral ranges from direct or indirect sunlight, or from other ambient white light. In specific aspects, the disclosure relates to a high quantum yield (QY) photoluminescent ambient light spectrum conversion device that is useful in various applications, including, without limitation, photodynamic therapy (PDT), low level light therapy (LLLT), as well as other biological applications, using sunlight and/or other ambient light to increase the energy provided in the 590-600 nm spectral range that can provide enhanced therapeutic properties by use of the disclosed spectrum converters.

DESCRIPTION OF THE RELATED ART

Currently available light spectrum conversion technologies provide relatively low overall light spectrum conversion efficiency and/or costly conversion of 360 nm-620 nm spectral range light into all or part of the Orange to Near-Infrared (ONIR) spectral range light (595-850 nm). The fluorescent and external phosphorescent quantum yield (QY) efficiencies of commercially available materials are typically less than 60%. Many dyes with high efficiencies are not stable enough for high luminance applications and have poor extinction coefficients in the desired spectral ranges, and thus require large quantities of dye when >80% of the incoming light is to be converted into the ONIR spectral range from Violet-to-Orange light (VIO). They are also high-cost relative to the most common conventional light emitting diode (LED) light sources for a given optical power output (in Optical Watts) and/or are characterized by other negative properties that lower overall spectrum conversion efficiency.

Current uses of fluorescent dyes and phosphors include printed fluorescent signs, paints, plastic products, fluorescent optical fibers, cathode ray tube and plasma televisions, biological and molecular tags, currency counterfeit protection, LED lights such as traffic lights, phosphor conversion of blue LEDs to white LEDs for visible lighting uses, display backlights, lighting of instrument panels, conversion of sunlight more into the ONIR spectrum to improve solar cell efficiency, enhancement of laser welding of plastics, and uses in many other applications.

A smaller number of light spectrum conversion intentional uses of light therapy exist, and these have been very simple implementations. Light converting products using light spectrum conversion have been proposed for light therapy with and without photosensitizers. The most prevalent use of spectrum conversion for light therapy is in Seasonal Therapy Disorder (SAD) systems that use white light, involving the conversion of blue LED light using one or more mixed phosphors and standard pre-coated phosphor LEDs similar to regular LEDs, but usually with extra blue and/or green light.

Cool white YAG:Ce phosphors are the most common phosphors used, and a small number also use a minor amount of orange 600 nm nitride phosphors or other lower cost and lower efficiency orange phosphors. Ambient light converters require alternate structures and materials, and have not been cost-efficient or practical using conventional technologies.

Up to 85% internal QY red phosphors are available at high cost, while lower cost red phosphors are under 60% internal QY. Additionally, light scattering by phosphor particles and absorption losses can cut the output light efficiency by another 20 to 50%, depending on the amount of phosphor used and overall design used due to internal scattering by phosphor particles and other losses.

When high percentages of the input short wavelength light are to be converted to the characteristic emission spectrum of the phosphor (e.g., when over 60% of output photons are to be in the phosphors' emission spectrum), the use of large amounts of phosphors can lead to poor quantum efficiency. Typical phosphors are therefore typically used at low concentrations in thin films so they transmit over ⅔ of the incident light (less than the above-discussed scattering and light absorption losses). Thin or low concentration layers of the phosphor in a polymer, e.g., silicone, matrix on blue LEDs is a common way in which these phosphors are used to produce warm-white light, typically converting less than a third of the blue LEDs' light output into the ONIR range. One of the biggest problems with phosphors has been that they work best and are most cost-effective when used at high concentrations in a small space such as a tiny dot directly on a LED. When the phosphor grains are separated by large distances, they are less likely to interact with photons. For ambient light applications, using these phosphors over large areas can be inefficient and very expensive.

Fluorescent dyes can have very low internal scattering losses in many transparent mediums since the dyes are molecular in size (as long as dye aggregation is minimal) and thus can achieve high spectrum conversion efficiency. A few red-emitting dyes exhibit over 90% QY; therefore, dye-based lamp systems can be two or more times as efficient as phosphor systems if over 60% of the light is to be converted to the ONIR spectrum. Fluorescent dyes are typically not used in LEDs, since it has not been possible to accomplish suitable photostability using available dyes in compatible media, and the Stokes shift is usually small so that most red emitters tend to absorb poorly in the violet-blue spectral region. Fluorescent dyes aggregate and lose efficiency when used at high concentrations, and thus are typically not well suited for use directly on LEDs. When matched to a correct medium, however, some fluorescent dyes are easy to dissolve and use in large area, high bulk volume applications.

Biological applications for fluorescent dyes, quantum dots, and phosphor-like nanoparticles include tagging and tracking of biological materials, and use as photosensitizers or photodiagnostic systems. Photoacoustic applications have also been reported. Most ONIR range photoluminescent materials are very expensive per gram of dye, characterized by low quantum yield, and/or provide poor stability in use. Fortunately, many dye applications do not require high photostability, high QY, and high extinction in the red to near-infrared spectral range. Unfortunately, minimal heat-producing, high-intensity light source applications do require all of such parameters to be simultaneously met.

Light therapy devices and methodologies that have been publicly reported or claimed include: (1) low level light therapy (LLLT) for treatment of inflammation and/or for tissue surfaces, other tissue healing, skin and tissue rejuvenation, muscle growth enhancement, muscle repair and pain reduction, accelerated tendon healing, joint or cartilage treatments, plantar fasciitis, pain management, traumatic brain injury (TBI) damage risk reduction, neurologic rejuvenation, enhancing stem cell generation, enhancing mood, enhancing healing rate of wounds, blood and body fluid treatments (with or without photosensitizers), spider vein and/or varicose vein and/or scar and/or stretch mark reduction treatments (with or without photosensitizers), reducing arterial plaques or other undesired biological materials using photosensitizers, treating biofilms on natural and/or man-made surfaces in or on the body, carpal tunnel, fibromyalgia, tendonitis, bursitis, tendonitis, migraines, osteoarthritis, dental root and implant healing or bone regrowth, enhancing the rate for other bone healing, accelerating T-cell life cycles and activity, accelerating macrophage action, veterinary applications, and/or providing other health-related medical benefits; (2) activation of photosensitizers used in photodynamic therapy (PDT) for cancer or antimicrobial treatments using natural or synthetic photosensitizers, including photosensitizers produced by bacteria in or on the body; (3) imaging and diagnostics using the emitted light spectral range; (4) intense pulsed light (IPL) therapies, sidereal or other mood therapies; (5) activation of adhesives or scaffolding agents as a part of reconstructive or cosmetic surgery; (6) photoactivation of release agents, e.g., to separate structures of compounds for surfaces; (7) powering of photocell-driven devices in the body; and/or (8) other uses such as light-sensitive chemical activation, and/or use of light therapy in combination with ultrasonic, vibration, thermal heating or cooling, and other combination therapies.

Non-therapy biological uses of light in the orange, red, and near-IR spectral ranges include: (1) enhancing plant growth, blooming, and/or ripening; (2) enhancing algae growth, photo-bacteria growth, and other photosynthesis and other photosensitive biological processes; (3) microbial stimulation; (4) increasing antimicrobial action on or in materials using photosensitizers (e.g., water or foods); and/or (5) visual image enhancement for enhanced detection of materials with unique light absorption and emission characteristics.

Even though the term "low level light therapy" or LLLT implies the use of low-intensity light, high-intensity light (>10 mW/cm$^2$ or even >1000 mW/cm$^2$) is usually desired to reduce the treatment time, or to obtain transmission of adequate intensities of red and NIR light into deep tissue, where the light intensity may be four orders of magnitude lower than at the surface of skin or other tissue. High-intensity light therapies usually refer to processes involving burning or extensive heating of tissue such as laser cutting. Near-infrared (NIR) light in the 750-840 nm range penetrates the most deeply through tissue of all visible wavelengths of light, but the intensity may be over 10,000 times lower at 6-8 centimeters below the skin surface than at the light source, depending on the type of tissue. Bone and cartilage are much more translucent to near-infrared light than most other tissue. Near-infrared light skin penetration is not significantly affected by melanin levels and skin color. Few products available to consumers or clinics provide the total absorbed light dose necessary for treatment over 4 cm deep in tissue and/or through living bone in less than 30 minutes time per location, and those that do require high power lamps and cooling capabilities. Higher intensity light provides minimum dose requirements at each depth more quickly.

The use of index coupling materials in contact with the skin can further increase the light transmission into the skin, as can minimizing the occurrence of air gaps between the skin and the light source. The nominal index or refraction of living skin for the 650-850 nm range, even taking racial or tanned skin pigment differences into account, is approximately 1.4. Extreme index of refraction variations still tend to still be within the 1.33-1.44 range. Several example solutions can be used for index matching, including ~25% gelatin:water mixtures, ~30% glycerin:water mixtures, ~35% sugar (e.g., sucrose):water mixtures, and several oils. Silicone gels have recently become available that can be customized to a wide range of refractive indices including 1.40, and these are non-liquid, highly-conformal and contact-safe materials. U.S. Pat. No. 6,096,066 describes matching index of refraction for a powered light emitting device.

All of the ONIR spectrum and the violet and blue light spectrum are present in natural sunlight. The goal of some electrically powered light therapies is to produce the equivalent ONIR dose of 2-4 hours of sunlight on selected parts of the body without the UV risk or waste in other wavelength ranges. These devices usually only produce part of the ONIR spectrum due to the narrow bandwidths of most LED or laser diodes, or generate huge amounts of heat when halogen lamps or other very high power light sources are used. A need exists for persons to be able to receive light therapy without powered sources while performing normal daily tasks, and with much less time in sunlight being required.

PDT therapies conducted using photosensitizers for actinic keratosis, skin cancers, acne, and other treatments frequently induce considerable pain after light exposure, because high power fast light treatments of photosensitizer treated areas conducted at clinics kill large number of cells quickly. Much slower red light exposures to photosensitizer activating light in the orange to red color light range can greatly reduce the pain. In Europe, many patients are sent out for sunlight exposure to activate photosensitizers, but this is not effective on cloudy days. If indirect sunlight and even office or home lighting could produce adequate amounts of red light, lower cost, less painful procedures could become possible.

SUMMARY

The present disclosure relates to a high quantum yield (QY) photoluminescent ambient light spectrum conversion device capable of absorbing and converting ambient light, including direct sunlight, into a modified light spectrum containing red and near-infrared wavelengths useful for light therapy or other applications. This device also passes much of the incident light in the spectral range in which the device's photoluminescent materials emit light, thereby greatly increasing the effective intensity of light available in the targeted 590-850 nm wavelength ranges. Certain embodiments of the present disclosure can also provide increased light intensity in the 400-460 nm spectral range that also has multiple therapeutic and biological uses. The approaches of the present disclosure can also provide significant reduction in ultraviolet spectrum light.

The passive device of the present disclosure creates red and near-infrared radiant light from shorter wavelength ambient light, and then adds this "new" light to existing red and near-infrared radiant light that can be transmitted to and into the tissue surface, thereby significantly increasing the red and near infra-red light available to the tissue from most types of bright ambient white light.

The device of the present disclosure can be designed to cover small areas, large areas, and custom shapes to cover large areas of the body or provide light to other special shape applications such as for medical, veterinary, horticulture, and research applications. Spectrum converters from under a square centimeter to many hundreds of square meters in size are practical using this device.

While light spectrum conversion using photoluminescent materials is known and widely used, the absorption and emission ranges, and efficiencies of the present approach and the flexible structure provide particular benefits for medical light therapy and/or other biological applications.

One important resulting aspect of the device of the present disclosure is the large absorption spectral range and the type of ONIR emission spectrum that this device creates. Light wavelengths covering all of the orange and red to near-IR spectrum are produced by this device using only ambient UV and white ambient light, and much of the incoming ONIR light passes through this device without interacting. The result is a device that absorbs light over the very large 360 nm to 590 nm spectral range with various embodiments also converting IR light into the ONIR spectral range to further increase the ONIR intensity. This device then emits light over the 590-850 nm range.

The photoluminescent materials used in this device minimally absorb light over most of this light emission range. To rephrase this important point, this matrix of synergistic phosphor and/or dye characteristics allows the device of the present disclosure to also absorb and efficiently concentrate sunlight or other white ambient light over a very large spectral range, and then add this energy to the already existing ambient light in the ONIR spectral range, and still reach the skin. The combination of this ambient ONIR light and generated ONIR light can provide over twice the intensity of ONIR light to the skin from sunlight and larger ONIR intensity multipliers from common office or household LED or fluorescent lighting sources. This device also blocks almost all UV light, making sunlight exposure substantially safer.

The device of the present disclosure can do more than only block UV light. Embodiments of this device also absorb UV light using selected phosphors, violet or blue dyes, and/or triphenylpyrazoline (TPP) as examples, and then convert a large amount of this absorbed UV light into useful violet or blue light with potential antimicrobial benefits. The device can be configured to transfer much of the violet light to the skin, and/or this violet and blue light can be converted by the ONIR spectrum converter into ONIR light to further increase the intensity of ONIR light into tissue.

For PDT applications, various embodiments of this disclosure can make slow exposures of tissue that has been topically treated using photosensitizers less painful than when higher light intensity fast light treatments are conducted in a clinic. Sunlight PDT treatments are becoming popular in Europe, but direct sun is not sufficiently available on cloudy days and daylight hours can be short in the winter in northern countries. The device of the present disclosure can intensify the available light at or near the excitation wavelengths of the photosensitizers used on cloudy days or in some well-lit home or office locations, and thereby permit acceptable delayed exposure treatments of photosensitizer-treated areas.

This device can also provide significant reduction in ultraviolet spectrum light. Several variations of absorption and emission spectra for photoluminescent filters including related materials and structures are hereinafter more fully described. Many portions of the 590-850 nm light spectrum are understood to provide multiple therapeutic benefits. Various articles employing the ambient light conversion approaches of the present disclosure are possible, including, without limitation, hats, visors, gloves, arm and wrist bands, other types of apparel, bandage-like patches, converting reflectors, large-area converters, awnings, and window covers. Horticultural and other photosynthesis-driven applications are also contemplated, as are spectrum-converting devices that can be shaped to cover light bulbs, and paint or spray-on coatings.

In one aspect, the present disclosure relates to a high quantum yield (QY) photoluminescent light spectrum conversion device for absorbing and converting sunlight and other available ambient light to a modified light spectrum output that contains 75% or more of its output radiant light spectrum in red, near-infrared, and/or infrared wavelengths, the device comprising two or more photoluminescent conversion materials that collectively absorb over 60% of normal angle ambient light entering the device in the 350 nm to 580 nm spectral range and the modified light spectrum output light emitted from within the device provides 75% or more of its output radiant light power in the 580 nm-850 nm spectral range, wherein the photoluminescent conversion materials are selected from the group consisting of dyes, phosphors, quantum dots, and photonic structures, wherein the device comprises one or more layers that are transmissive of at least 40% of normal angle ambient light in a spectral range of over 600 nm entering the device, and wherein the device does not utilize any electrical power supply for the production of the modified light spectrum output.

In another aspect, the disclosure relates to a method of light therapy treatment of a subject in need thereof, such method comprising generating a modified light spectrum output using a device according to the present disclosure, and exposing a body region of the subject to the modified light spectrum output.

Additional aspects, features and embodiments of the disclosure will be more fully apparent from the ensuing description and appended claims.

DETAILED DESCRIPTION

The present disclosure relates to photoluminescent ambient light spectrum conversion devices configured to absorb and convert ambient light, including direct sunlight, into a modified light spectrum containing red and near-infrared wavelengths useful for light therapy or other applications.

As used herein, the singular forms "a", "an", and "the" include plural referents unless the context clearly dictates otherwise.

Although specific embodiments of the disclosure are shown and described in detail hereinafter, it will be understood that various additional changes and modifications not specifically described herein may be made without departing from the scope of the disclosure hereof. The scope of the present disclosure is not intended to be limited in any manner with respect to the number of constituting components, the materials thereof, the shapes thereof, the relative arrangements thereof, etc., and specific implementations are disclosed simply as examples of potential embodiments within the scope of the disclosure.

Other aspects, embodiments and features of the present disclosure will become apparent from the detailed description and/or when considered in conjunction with the accompanying drawings. Some, but not all, features and advantages are illustrated in the accompanying drawings. The accompanying figures are schematic and are not intended to be drawn to scale. For purposes of clarity, not every component is labeled in every figure. Nor is every component of each embodiment shown where illustration is not necessary to allow those of ordinary skill in the art to understand the disclosure.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure contemplates such features, aspects and embodiments in various permutations and combinations, as being within the scope of the disclosure. The disclosed subject matter may therefore be specified as comprising, consisting or consisting essentially of, any of such combinations and permutations of these specific features, aspects and embodiments, or a selected one or ones thereof.

As used herein, the following technical terms have the following meanings:

"about" in reference to a specific numerical value refers to a range of ±10% of such specific numerical value.

"nm" means nanometers ($10^{-9}$ meters length or size).

"micron" means micrometers ($10^{-6}$ meters length or size).

"Dye" means fluorescent or phosphorescent material(s) that are mostly distributed at a molecular level in solutions (e.g., polymers, sol gels, low temperature glasses, liquids or gels, and other translucent materials in a wide variety of shapes). Dyes may aggregate into groups of molecules, remain separate in the medium, and frequently contain some combination of both dye aggregates and non-aggregated dye molecules.

"Low-temperature melting glass (LT Glass)" refers to a low temperature melting glass with a transition temperature typically below 450° C. if it is to be used with organic dyes. For use with phosphors, the transition temperature can be much higher, depending on the phosphor used.

"Matrix" or "medium" refers to a material that is mostly translucent to the absorption and emission wavelengths of the photoluminescent materials that are placed in that material. These medium materials can be in the form of coatings, sheets, bulk materials, molded or otherwise shaped materials, or liquids in a cavity. These materials may comprise, consist, or consist essentially of, organic and/or silicone polymers, glasses, crystals, microstructured or nanostructured arrays, multilayered structured materials, inorganic composites, inorganic and organic composites, sol gels, liquid crystals, and many other materials. The medium materials may be in the form of solids, semisolids, chalcogenides, gels, liquids, liquid crystals, and/or combinations thereof.

"OCST": Other spectrum shifting technologies: OCST include photonic crystals, quantum dots (QDs), photonic spectrum converting fibers, photoluminescent fibers, and/or crystal arrays or matrices including combinations of these and other spectrum converting technologies.

"PDT" means photodynamic therapy or the use of light as part of a therapy or diagnostic procedure. In this disclosure we will only refer to PDT as light therapy using photosensitizers.

"Photoluminescent" means a characteristic of light of one spectral range being first absorbed by a material, and all or part of this absorbed energy being subsequently emitted to provide a different spectrum of wavelengths. This term's definition broadly includes both fluorescence and phosphorescence characteristics.

"PS" means photosensitizer, a compound or particle that absorbs light and initiates or engages in chemical reactions using the light energy.

"Phosphor" refers generally to inorganic photoluminescent materials (fluorescent or phosphorescent) that are usually used as small crystalline particles, crystallites or fibers that appear like a powder before mixing. In this disclosure, for simplicity we generalize the use of "phosphor" to cover all particle-based photoluminescent materials, which includes quantum dots, unless quantum dots are specifically separately mentioned. These materials are mixed and suspended in a variety of polymers and other transparent and translucent medium materials such as silicones, silicates, sol gels, polymers, etc., and can be painted on surfaces or shaped into structures such as lenses or sheets. Phosphors can also be deposited as thin films on surfaces without a medium or matrix material. All compositions and forms of these materials and mixtures of these materials, are termed phosphor in this disclosure.

"Reporter" means photoluminescent compounds or particles that absorb one spectrum of light and emit another spectrum of light, generally used to assess the presence and/or concentration of a photoluminescent material and 'report' this information to optical sensors (or acoustic sensors, when photo-acoustic reporters are used).

"Quantum Dots" are nanoparticles with multiple layers instead of single composition crystal particles as in phosphors. As photoluminescent materials, quantum dots behave similarly to phosphors, but can be more efficient; highly selected QDs of the same structure can exhibit more narrow emission spectra.

"Quantum yield" means the ratio of emitted photons/absorbed photons from a material for a specific excitation spectrum. It is shown as percentage without units.

"$\epsilon$" means extinction coefficient, in $M^{-1}cm^{-1}$. "Extinction" shown as the symbol epsilon ($\epsilon$) refers to the probability of a dye or other material absorbing photons at a specific wavelength. A higher number means a higher probability of absorbing photons at a wavelength. If a reference wavelength is not explicitly specified, it is assumed that the extinction coefficient refers to the maximum major extinction or absorption peak that is shorter wavelength than the maximum emission peak for the photoluminescent material. "Extinction" does not directly apply to some materials, even though all photoluminescent materials exhibit similar photo-optical characteristics, so "effective extinction" may be referred to in some relative contexts.

"ONIR" means orange to near-infrared spectral range light (595-860 nm) While many information sources consider near infra-red light to extend past 900 nm, we have confined the ONIR range for the specific applications herein to be 595-860 nm.

"IR" means infrared, and is applied to light in a spectral range above 860 nm.

"NIR" means near-infrared and is applied to light in the 720-860 nm range (slightly visible to most persons even at moderate intensities).

"Red" means 620-720 nm light.

"Orange" means 595-620 nm light.

"UV" means ultraviolet light with wavelengths in the 100-400 nm range.

"UVA" means ultraviolet light with wavelengths in the 315-400 nm range.

"UVB" means ultraviolet light with wavelengths in the 280-315 nm range.

"VIO" means violet to orange spectral range light (385-620 nm).

"VIY" means violet to yellow spectral range light (385-650 nm).

"Violet spectral range" means 385-435 nm.

The present disclosure provides a high quantum yield (QY) photoluminescent ambient light spectrum conversion device capable of absorbing and converting ambient light, including direct sunlight, into a modified light spectrum containing red and near-infrared wavelengths useful for light therapy or other applications. This device also passes much of the incident light in the spectral range where the device's photoluminescent materials emit light, thereby greatly increasing the effective intensity of light available in the targeted 590-850 nm wavelength ranges. Certain embodiments of this device can also provide increased light intensity in the 400-460 nm spectral range that also has multiple therapeutic and biological uses. This device can also provide significant reduction in ultraviolet spectrum light.

The device of the present disclosure is primarily comprised of one or more photoluminescent spectrum conversion layers with a unique combination of chromophores that absorb light over the entire UV to visible wavelength range and provides 590 nm to 850 nm spectral range light with high efficiencies and minimal reabsorption. The conversion layers can be either phosphors or dyes, including dyes in polymeric solutions.

In one embodiment of the present disclosure, the light source contains one or more dichroic filter(s) placed either above, between, or below the spectrum conversion layers.

In one embodiment of this disclosure, one or more up-converting phosphors are added to one or more of the device layers to convert infrared light into red light and/or near-IR light with the majority of the spectral range being below 850 nm. This permits the IR component of sunlight to further intensify the ONIR intensity without increasing the overall radiant energy density on the skin, thereby increasing the therapeutic dose rate of ONIR light without increasing the heat load to the skin (as compared to sunlight exposure in the absence of the device of the present disclosure). This is also a benefit for many non-therapeutic biological applications.

Embodiments of this device may be used for PDT photosensitizer activation, and for other uses with similar ONIR light dose requirements. These embodiments can be fabricated with just the dyes, phosphors, or quantum dots producing the light spectra close to the absorption peaks of the specific photosensitizers being used. For the most common photosensitizers being used in clinical dermatology, these peak wavelengths are about 630 nm, 650 nm, 665 nm, and 690 nm. One preferred implementation comprises the perylene and perylene-derivative dye embodiments of this disclosure, wherein the dye is selected to match the photosensitizer used. However, phosphor, quantum dots, and mixed spectrum converter embodiments of this disclosure can also be employed, as highly effective, but more expensive. Additionally, providing near-IR in the spectrum to a treated area would have almost no effect on currently approved photosensitizers that are not sensitized to near-IR light, and may provide further benefit to the healing process.

The structure of a PDT photosensitizer activation device, as well as for other uses and applications having similar ONIR light dose requirements, suitably comprises an adhesive bandage-like patch placed over the treated area. Sheets of material in various embodiments of this disclosure can be cut to fit the area to be exposed, and the perimeter of the device can be taped in place, or the device may be directly made adherent to the skin, with or without a silicone, or a breathable, fabric or paper-like, mostly translucent, covering between the skin and the spectrum converter layer. Alternatively, preformed bandage-like patches can be made in various sizes to fit over the area to be treated, with adhesives in or around the device, or without adhesives so they can be taped on to the body or otherwise held in place. The present disclosure contemplates incorporation of the device in applications including, but not limited to, medical bandages, straps, body-wraps, or bands, comprising spectrum converter(s) and/or filters configured to provide therapeutic light to areas of the skin. Furthermore, adhesion may be provided by perimeter adhesives, transparent adhesives, straps, elastic or rubber-like bands, or the device may simply be held in place manually or otherwise.

If a significant increase in light intensity occurs while a PDT patient is wearing the device, such as when the sun coming out, an adherent filter can be placed over the device using adhesive or tape, to reduce the light intensity back to the level of cloudy day conditions, or the device can be covered by any material opaque to UV and visible light, to stop the PDT process.

In another embodiment for PDT and other uses with similar requirements, a small photosensitive chemical patch that changes spectrum after a sufficient total light dose is received, or a small solar cell-like sensor, can be attached to the device to provide feedback regarding the total light dose received by the patient. The patient can then know when an adequate amount of light has been received, and can also know how close they are to completing the necessary light dose for their PDT treatment. The light sensor can be placed under the light conversion device, to detect the total converted light received, or near the device with conversion over the sensor, or the sensor can be calibrated to indicate when proper under the spectrum converter, even if the sensor is not under the spectrum converter.

In additional specific embodiments, a customized 1.4 refractive index rubber silicone gel material, e.g., NuSil™, or other ~1.4 refractive index polymer(s), may be arranged to be in direct contact with the skin. This silicone gel is a solid gel that exhibits structural integrity, and is not a semi-solid like gel, although cream-like gels are also contemplated within the broad scope of the present disclosure. This silicone gel pad can be a permanent part of this device, or it can be removable and replaceable, or it can just be placed as a thin pad between the skin and the spectrum converter device. Translucent, food grade or higher, silicones with hardness of less than Durometer 20 are preferred for the portion of the silicone facing the skin, unless compression or other pressure is used to press the light therapy device against the skin. Minimal light coupling losses due to air spaces between the light therapy device and skin can be achieved using flexible and conformal or body-contoured bandages as described herein.

In another embodiment of this device suitable for placement on the skin, phosphors, QDs, or dyes are dispersed in a gel that may be used on the area to be treated, to convert short wavelength light (e.g., light predominantly under 610 nm) into red and near-infrared light predominantly over 600 nm. The gel then will act as the spectrum converter, or as one or more of a grouping of spectrum converters, or as a component of the spectrum converter. Mixtures and multiple layers of spectrum converter materials are contemplated within the broad scope of the present disclosure.

Suitable gels may be semi-liquid and/or semi-solid materials when applied to the skin, such as petroleum jelly, silicone grease gels, starch pastes, protein or amino acid and water or oil mixes, fats, many emoluments, polyvinyl alcohol, many hydrogenated or thickened oils or fats, waxes, paraffin, oil and transparent particle emulsions such as mica and vegetable oil, gelatins, and/or other materials. The gels may also be semisolid and exhibit structural integrity similar to that of low 10 Durometer silicones or transparent putty-like materials such as some rubbers. Gels that are applied to the area to be treated as liquids or gels and then can harden into a semisolid or even a rigid film after application, such as some epoxies, rubber cements, and similar materials, are also contemplated within the broad scope of the present disclosure.

These gel materials may be placed directly on the skin or tissue if they are compatible with direct skin or other relevant tissue exposure, or one or more thin translucent films or sheets such as a silicone or other polymer may be placed on the skin under the spectrum converting gel to prevent direct contact between the skin and the gel, if desired.

The gel may be used on the skin or a skin-covering by itself and then washed or rubbed off, or it may be encapsulated for a period of time with a translucent blister-like coating, cover, or polymer.

Dyes not soluble in a selected gel medium may be formed into particles of many possible shape configurations and dispersed in the medium. An example is the disclosed perylene related dyes dispersed in polycarbonate to be formed into small particles. Many methods exist to form particles from dyes in plastics or other media, including spraying the heated or a pre-polymerized mixture into inert gas, air, or a vacuum, extruding and cutting, grinding the medium-dye mix, or dispersing the medium and dye mix in a liquid where it can form particles. PMMA, polycarbonate, several low temperature glasses, and/or other materials are known as good media for these dyes. Other dyes or photoluminescent materials may require other media for optical performance.

Oriented spectrum converters can provide an advantage by directing more converter red and near-IR light at the skin. Placing certain spectrum converter films in a high electric field while the film is heated near or above the glass transition point, or while the film is first setting into a solid, can establish a preferred orientation of many molecular dyes and provide a preferred light emission direction. This technique is known for use in some fiber optic systems with dyes, but is novel in the applications of the present disclosure.

Long-pass optical filters or reflectors formed as films or effectively as sheets or layers may be placed in the light path so that light that passes through the spectrum converters and then these filters or reflectors. Shorter wavelength light in various applications can be reflected back up into the spectrum converter by suitable reflector element(s) and arrangements, for renewed opportunity for conversion.

In still another embodiment, minors and/or non-specular reflectors can be made using the spectrum converting device by laminating the spectrum converter to the reflector. Reflectors can be of any suitable configuration, for example, either flat and rigid, or flexible and shaped as concentrators. The reflector or non-specular reflector embodiments can be used in a manner similar to tanning mirrors, to further concentrate ONIR and/or violet and/or blue light, but without the UV tanning effect. Such spectrum converting mirrors or films can also be used to enhance lighting in greenhouses, and in other horticulture applications, in enhancing biomass, algae, and/or photobacteria growth, as intensifiers for solar cells, as well as applications such as concentrating red, NIR, and/or ONIR light in or into optical fibers, generating suitable light outputs in other light channeling structures and/or other materials, and in many other applications.

Window coverings, wall coverings, awnings, umbrellas, liners in various structures, and other architectural and portable items are potential applications and usages of either reflector or translucent embodiments of this invention. On windows, ambient light conversion devices of the disclosure can be used to change the light spectrum, and can be used in various applications to additionally partially obscure vision through windows, especially at shallow angles. Adding other dyes to the primary or secondary converters of this device, such as BASF 083 Yellow, BASF Red 305, and/or BASF Orange 240 perylene dyes, along with phosphors and absorbing or photoluminescent pigments, permits the reflected, re-emitted, and/or transmitted spectra and the amount of light that is absorbed, re-emitted, or transmitted, to be adjusted over a wide range of effects on windows, reflective surfaces, and other surfaces. The concentrations and types of dyes, quantum dots, or phosphors used can be modified to optimize the mix of converted and unconverted light to match the objectives of lighting designers, architects, and individuals. Flooding spaces with increased intensities of violet, blue and/or all or portions of the ONIR spectrum can be utilized to provide interior and exterior aesthetic effects, and provide additional light intensity where human vision is weaker, and/or to enhance indoor plant growth and blooming, and/or to provide potential health benefits in such spaces or environments.

In other embodiments, spectrum converting devices of the present disclosure can be shaped for placement over coverings (e.g., housings or enclosures) for lighting articles such as fluorescent bulbs.

In still other embodiments, ambient light conversion devices of the present invention can be created, using a paint or spray-on coating. The disclosed perylene and perylene derivative dyes are soluble in acetone and several other solvents, and may be usefully employed for this purpose. Phosphors are more expensive, but can be dispersed like pigments. Numerous embodiments of this disclosure can be prepared as coated or applied film materials, using a variety of coating technologies.

The ensuing discussion is directed to detailed descriptions of specific preferred embodiments.

According to one aspect of the present disclosure, there is provided an ambient light conversion device, including a sheet of material and/or coated material, of one or more layers, wherein one or more layers contain phosphor(s), fluorescent dye(s), phosphorescent dye(s), photonic crystal-like array(s), doped or photonic converting fiber array(s), or quantum dots that can absorb most of the ultraviolet, violet, blue, green, and yellow light entering the ambient light conversion device, with no, low, or moderate light re-adsorption between the photoluminescent materials in the matrix. This spectrum converter device then efficiently converts this light into the ONIR spectral range, with an option for allowing a controlled portion of the violet light to pass. This device also provides a hard (>99%) cutoff below 390 nm by moving the UVA energy into the violet or blue, and not only by reflecting or absorbing and thereby wasting this energy.

In such ambient light conversion devices, various unique combinations of photoluminescent materials and spectrum conversion layer matrix arrangements are contemplated, within the scope of the present disclosure.

In one aspect, the present disclosure relates to a high quantum yield (QY) photoluminescent light spectrum conversion device for absorbing and converting sunlight and other available ambient light to a modified light spectrum output that contains over 60% its output radiant light spectrum in red and near-infrared wavelengths, the device comprising two or more photoluminescent conversion materials that collectively absorb over 40% of ambient light entering the device in the 350 nm to 580 nm spectral range at up to 50 mW/cm$^2$ incident light power, and the modified light spectrum output of the device when supplied with 5 mW/cm$^2$ ambient light in the 350 nm-580 nm spectral range provides over 60% of its output power in the 580 nm-850 nm spectral range, wherein the photoluminescent conversion materials are selected from the group consisting of dyes, phosphors, quantum dots, and photonic structures, wherein the device comprises one or more layers that are transmissive of at least 40% of ambient light in a spectral range of over 600 nm entering the device, and wherein the device does not utilize any electrical power supply for the production of the modified light spectrum output.

The device of the present disclosure produces the modified light spectrum output at wavelengths useful for light therapy and other applications. The device utilizes no electrical power for the production of the modified light spectrum output, and therefore requires no electrical power supply as a component of the device. The device may be fabricated as comprising multiple layer materials, at least some of which contain photoluminescent conversion material(s), and the device in various embodiments may comprise a laminate sheet-form or web-form structure. The device is fabricated so that it is light transmissive, and the one or more layers of the device may be correspondingly transparent or translucent in character as appropriate to satisfy the light transmissivity criterion described above.

The device of the present disclosure may be fabricated with the photoluminescent conversion materials comprising layers or mixtures including: a violet-UV absorber and violet-blue light emitter photoluminescent dye; a violet-blue absorber and blue-yellow light emitter photoluminescent dye; a green-yellow absorber and orange and/or red light emitter photoluminescent dye; and optionally a blue-green absorber and yellow-orange light emitter photoluminescent dye. The photoluminescent conversion materials may be used as a layered grouping and/or a mixture of dyes, wherein the various adsorber and emitter materials may in specific embodiments comprise the following specific conversion species: violet-UV absorber and violet-blue light emitter materials such as BASF Lumogen F Violet-570 (naphthalimide), BASF Lumogen F Blue-650 (naphthalimide), BASF Uvinul, Tinopal OB brightener (2,5-thiophenediylbis(5-tert-butyl-1,3-benzoxazole)), and/or triphenylpyrazoline (TPP); violet-blue absorber and blue-yellow light emitter materials such as BASF Lumogen F Yellow 083 and/or Yellow 170; blue-green absorber and yellow-orange light emitter materials such as BASF Lumogen F Orange 240; and green-yellow absorber and orange and/or red light emitter materials such as BASF Lumogen F Red 300 and/or Lumogen F Red 305, and/or perylene chemistry-related derivatives, such as OR165, OR645, OR670 and/or OR775. The aforementioned materials may be mixed into a single layer, mixed into some of multiple layers, not mixed and provided in separate layers, and/or used in multiple layers, e.g., 4 or more layers in a "stack", or in which layers of material repeat in a stack or repeat in some layers as different mixtures containing one or more same absorber and emitter species.

In the foregoing arrangement of photoluminescent conversion materials, one or more of the photoluminescent dye materials in one or more layers may be substituted with or supplemented with material, selected from the group consisting of phosphors and quantum dots, that absorb in the violet and/or blue, and that emit primarily in the red and/or near-IR spectral region. Examples of suitable phosphors and QDs include nitride and oxynitride phosphors with 580 nm or higher emission, and preferably with emission at 650 nm or higher.

In various embodiments of the device of the present disclosure, the photoluminescent conversion materials may be coated on or overlie a mirror or non-specular reflective surface.

In specific embodiments, the device may further comprise a monitoring assembly comprising at least one photosensor and configured to generate an output indicative of at least one of dose status, progress of dosing, and completion of dosing, of the modified light spectrum output of the device. Thus, one or more photosensors may be used to provide a user or attendant with information regarding direct or indirect dose status of the light treatment and/or when specific light dosages at certain wavelength ranges have been completed. The monitoring assembly may for example include one or more electronic photocells connected to an electrical monitoring device or system to assess when a specific dose has been administered, and optionally provide notification to a user or attendant, record the time vs. light treatment conditions over the period of light treatment exposure, and/or optionally record other data from other sensors such as temperature at one or more points. Additionally, or alternatively, the monitoring assembly may comprise photosensors located on or near surfaces being radiated, and/or at other points in or near the device.

The device in certain embodiments may comprise an optical filter transmissive of ambient light in the red or near infrared range, so that it constitutes a portion of the output radiant light spectrum. For example, the device may comprise one or more photocell devices with one or more notch and/or long-pass optical filter for use in the red or near infrared spectral range, and/or other photosensors for assessing the incident light at or near the photocell(s), and/or for assessing other conditions such as the status of a photosensitizer, an administered drug, or skin condition of the user.

The device of the disclosure may comprise a light control assembly that is configured to: (i) increase or decrease light passing though the device; (ii) deactivate the device, or otherwise reduce or block light coming from the device to the target surfaces when a predetermined light dose level of the modified light spectrum output of the device has been reached; (iii) modulate intensity of the modified light spectrum output of the device in response to variable ambient light radiant intensity; and/or (iv) execute a light dose vs. time regimen for the modified light spectrum output of the device. Such light control assembly may comprise electronically controlled light valves, electro-chromic devices, and/or suitable LCDs, including ferroelectric LCDs.

The device in various embodiments may comprise a monitoring material that upon a predetermined exposure to ambient light or spectral region(s) thereof changes optical density and/or color to provide a visually discernible indication of status and/or completion of light dosage from the device. For example, one or more light sensitive dyes and/or other materials may be disposed on and/or near the main body of the device, which are constituted to change optical density or color after exposure to some or all or portions of the red and near-IR spectrum and/or all or some parts of the incident light spectrum. Such sensor can provides a visual notification of the status of and/or the completion of a designated light dose.

In various embodiments, the device may comprise a dose-limiting material that upon a predetermined exposure to ambient light or spectral region(s) thereof changes optical density to provide a predetermined light dosage of the modified light spectrum output of the device. For example, one or more light sensitive dyes and/or other materials in layers or mixtures can be provided in the light path of the device, with such dye(s) and/or material(s) increasing their optical density with light exposure so as to predictably increase or reduce the radiant light power exiting the device so that the device provides a specified therapeutic input light intensity. For this purpose, a light blocking material may be employed that is resettable, removable, or replaceable, permitting future additional exposure doses.

In some specific embodiments, the device may comprise a bandage structure incorporating the photoluminescent conversion materials and configured for application to the body of a subject for administration of the modified light spectrum output of the device, optionally further comprising an insert to be interposed between the body of the subject and the bandage structure, wherein the insert has an index of refraction matched to a surface of the body to be treated, and is adapted to therapeutically augment the administration of the modified light spectrum output of the device. For example, the device may be configured similarly to a bandage, with an optional transparent top surface and/or transparent bottom surface, in contact with or in close proximity to a surface to be exposed with red and/or near IR light. Such bandage may be large or small area, adherent to the surface, be arranged to be strapped on, or just held in place during use. If one or more materials are inserted between the device and the surface to be exposed to light exiting the device, the materials may comprise materials having a similar index of refraction to the surface, to provide therapeutic benefits in light therapy, such as pain reduction, antimicrobial functions, administration of emollients, aiding of oxygen transfer or reducing oxygen, heating and/or cooling, and/or providing a comfortable patient skin or tissue interface for medical applications.

The photoluminescent light spectrum conversion device of the disclosure in various embodiments may be configured as a gel, cream, liquid, semisolid, or a state converting material containing the photoluminescent conversion materials. For example, the device may comprise liquid in a bladder, or a state converting material such as a hardening gel or putty with an optional transparent surface and/or transparent bottom surface, in contact with or in close proximity to the surface to be exposed with red and/or near IR light.

The photoluminescent light spectrum conversion device of the disclosure in various embodiments may further comprise at least one reflector arranged to reflect light to the photoluminescent conversion materials for enhanced conversion to the modified light spectrum output, and optionally further comprise at least one filter arranged to transmit reflected light in the spectral region of the modified light spectrum output, to the output. For such purpose, the device may be arranged with long-pass optical filters or reflectors formed as films, sheets, or layers that may be placed in the light path so that light that passes through the photoluminescent spectrum converters and then to the long-pass filters or reflectors. Shorter wavelength light will be reflected back into the photoluminescent spectrum converters for a further opportunity for conversion, while longer wavelength light can pass out of the device for use. Suitable filters and mirrors include interference filters, which may be planar, curved and/or have three-dimensional optical element shapes.

In various embodiments of the photoluminescent light spectrum conversion device, one or more of the photoluminescent conversion materials is spatially oriented to enhance the intensity of the modified light spectrum output. Such oriented character may for example be employed to provide an output light intensity advantage by directing more of the converted red and near-IR light at the target surfaces.

One or more of the photoluminescent conversion materials in the photoluminescent light spectrum conversion device of the disclosure may be comprised in an array of optical fibers. Such optical fiber arrangement may be advantageously employed, for example, to increase light output, change the output angle characteristics, or to better couple the output into a fiber optic system.

In various embodiments of the device, one or more of the photoluminescent conversion materials may be comprised in one or more layers of applied coatings or laminate articles. The applied coatings may for example comprise one or more layers of spray-coated paints and/or laminate layers on a suitable substrate article, e.g., a translucent material or coated mirror. Applications that may be accommodated with such devices include use of the photoluminescent light spectrum conversion device in greenhouses, in indoor and outdoor plant growth enhancement areas, and for improving domestic lighting for plants, for modifying plant budding, blooming and ripening, for increasing the therapeutic value of general lighting from ambient light entering and/or existing in buildings, for external or internal cosmetic appearance reasons, and/or for general architectural purposes. The photoluminescent light spectrum conversion devices in these or other applications can be formed as windows, lamp coverings, (translucent) panels, attachments to lamps and/or LED displays, and as arrays, e.g., of translucent spectrum converter panels or coated mirror panels.

The photoluminescent conversion device in various embodiments may comprise fibers or fabric, comprising or coated with one or more of the photoluminescent conversion materials. For example, the device may comprise fibers formed of materials such as acrylics or nylons or other polymers or fiber materials, comprising or coated with photoluminescent conversion materials, including multiple coats if desired. Such fibers (threads) can be used to provide apparel articles, such as pants, dresses, shirts, coats, jackets, shoes, gloves, arm or leg bands, coats, hats, visors, and other accessories. Also, other fabric based products may be made using these devices, such as umbrellas, blankets, wraps for parts of the body, tents, physical therapy braces and wraps, face covers, and other articles. In specific applications of such types, the photoluminescent conversion materials may include dye or phosphor mixtures in polymer fibers or as one or more coatings on synthetic or natural fibers. Polyimide, polyester, nylon, aluminum, cotton, wool, and other fiber-based fabrics are contemplated, as are optical fibers, and arrays of optical fibers.

The photoluminescent conversion device in various embodiments may comprise a sheet, film, molded, moldable, or web article, comprising or coated with one or more of the photoluminescent conversion materials. Such sheets or films may be optionally laminated, painted onto, or formed into sheets of spectrum-converter materials, as well as moldable materials such as silicone rubber. Again, such materials may be employed to fabricate dressing apparel, such as pants, dresses, shirts, jackets, coats, shoes, gloves, arm and leg bands, hats, visors, and other accessories. Additionally, other fabric, plastic sheet, and rubber-based products may be made using these devices, such as umbrellas, blankets, wraps for parts of the body, tents, physical therapy braces and wraps, face covers, and other articles. In specific applications of such types, the photoluminescent conversion materials may include dye or phosphor mixtures coated onto sheets of material, e.g., on porous membranes or other sheet material, or formed as its own sheet material, or in or on fibers coated with aluminum or other reflector material including for example dichroic reflector material.

The photoluminescent light spectrum conversion device of the disclosure may in various embodiments be disposed in light-supplying relationship to provide the modified light spectrum output to a light-utilizing system, wherein the light-utilizing system comprises a system selected from the group consisting of: botanical plant growth systems, algae growth systems, systems for the purification of water or body fluids, and systems for antimicrobial treatment of water or body fluids. Such applications may utilize added photosensitizer in various specific embodiments, or alternatively be implemented without the use of added photosensitizer.

The disclosure further contemplates a method of light therapy treatment of a subject in need thereof, such method comprising generating a modified light spectrum output using a photoluminescent light spectrum conversion device of the present disclosure, and exposing a body region of the subject to the modified light spectrum output. For such treatment, the photoluminescent light spectrum conversion device(s) may be positioned using straps, adhesives, gels, and/or other materials and/or techniques to maintain the device(s) positioned correctly for duration of the light therapy treatment. The light therapy treatment may be carried out to treat: joints and muscles for reducing pain and inflammation; wounds fix improving the rate of wound healing acne, rosacea, skin tone, and other dermatological conditions, to improve healing, and reduce the population of bacteria or fungus that are directly or indirectly photosensitive to the light spectrum of the light therapy treatment; muscles for enhancing regeneration of tissue after exercise or other stress; bone areas to repair damage and improve bone density; or head, neck, spine, or other body areas, for pain and inflammation, for mood treatments, for reducing damage from brain injuries, or for increasing generation of nerve stem cells. For the light therapy treatment, the photoluminescent light spectrum conversion device(s) may be positioned on, over, near, and/or around the body part to be treated. Subjects treatable by the light therapy treatment of the present disclosure include human as well as non-human (e.g., mammalian or other veterinary) subjects.

Figure 1:
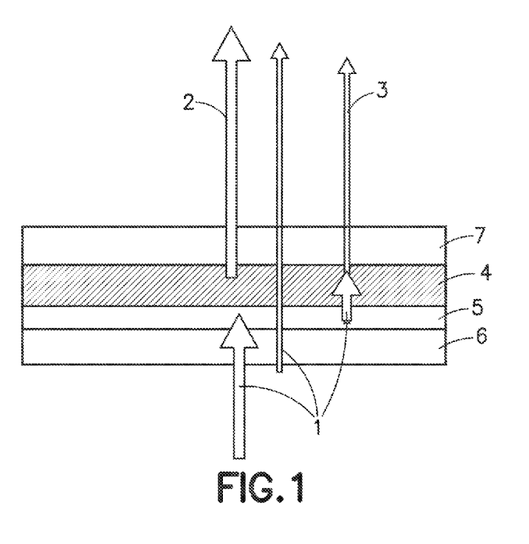
FIG. 1 is a schematic representation of a spectrum converter for ambient light according to one embodiment of the disclosure, comprising a transmissive photoluminescent converter ("Embodiment 1").

Referring now to the drawings, FIG. 1 is a schematic representation of a spectrum converter for ambient light according to one embodiment of the present disclosure, comprising a transmissive photoluminescent converter ("Embodiment 1"). This embodiment is advantageously employed to maximize ONIR light output from ambient sunlight. The ambient light converter device may be fabricated, using a sequence of non-toxic organic dyes is selected that can put into solution in a variety of polymers.

In FIG. 1, two arrows 1 pointing into the device represent incoming sunlight or other bright ambient white light. The arrow that passes completely through the device represents unconverted visible incoming light, which is typically under 10% for this exemplified device. The upper arrow 2 pointing out of the device represents converted ONIR light exiting the device. The two-part arrow 3 originating in the device represents violet and blue light from the UV converter layer that is at least partly converted to ONIR, which can be a >90% conversion as well.

The middle sheet 4 of this device is 0.01-1 mm thick polycarbonate containing 0.1-10% polyvinyl chloride (PVC). This sheet is doped with TTP, BASF Yellow083, BASF Red305, OR670, OR775, and optionally OR820.

Unnecessary multiple reabsorptions are uniquely avoided in this photoluminescent materials matrix, while still providing high absorption across the spectral range and high-efficiency energy transfer paths to move energy into the ONIR range. The aforementioned dyes also exhibit unique efficiency effects together, indicating that there may be non-photon energy exchanges occurring between similar molecules. This effect is enhanced by not providing a simple energy transfer ladder.

The device of Embodiment 1 is not a simple phosphor pump or phosphor ladder. The only absorption and emission peak match is between BASF 083 and BASF 305, and the concentration of BASF 083 is typically kept 4-6 times lower than the other dyes in this arrangement, so that the BASF Red305 pulls most of its energy from new incoming photons and from the TPP or the Violet 570 components.

The concentrations of these dyes can all be in the 0.001-0.3% (wt %) concentration range, with specific concentrations being selected based on the spectral shape desired. The medium containing the dyes can have a matte finish and the thickness of sheet 4 should be under 0.35 mm for good flexibility, if a reasonably conformable color converter is an objective.

Referring still to FIG. 1, the next layer 5 can be coated or laminated to sheet 4. Several acceptable polymer media for 5 exist. PMMA in acetone is suitable for painting, or thin flexible acrylic sheet between 0.05 and 0.4 mm thickness can be used. Triphenylpyrazoline (TPP) and BASF 570 are added in a 1-0.01% range of concentration. The lower layer 6 is optional and can be any number of films or coatings. One preferred film is transparent potting silicone mixed 1:1 with a Durometer 50 hardness silicone material at a thickness of 0.01-0.1 mm thickness. In the lower film a 1-12% Intermatix 650 nm oxynitride phosphor can be added into one of the silicone components before mixing and curing, to boost output efficiency. The optional top layer 7 of the device is a protective layer and can comprise a highly transparent silicone material like the lower layer. This layer 7 can be undoped and can comprise the same silicone material as the bottom layer 6, although many other materials may be employed in such layer.

A variation of Embodiment 1 comprises addition of up-converting IR phosphors to the layer 6 to further increase the ONIR light output. A 1-12% concentration of 980 nm emitting phosphor can be employed, although this phosphor and other up-emitting phosphors can be added in other layers or additional layers and structures in the device.

Figure 2:
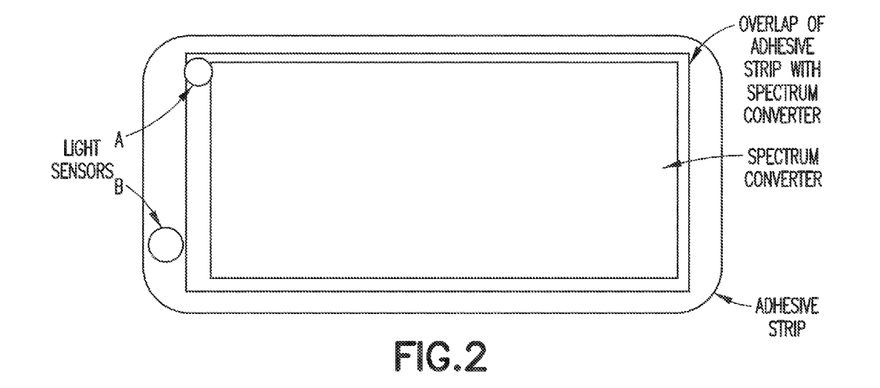
FIG. 2 is a schematic top plan view of a spectrum converter for ambient light according to another embodiment of the disclosure, comprising a spectrum converter useful for photodynamic therapy ("Embodiment 2").

FIG. 2 is a schematic top plan view of a spectrum converter for ambient light according to another embodiment of the disclosure, comprising a spectrum converter useful for photodynamic therapy ("Embodiment 2").

In FIG. 2, a top view of a bandage-style device for PDT is illustrated. This device can be similar in cross sectional detail to Embodiment 1, but with an adhesive perimeter added. Tape and other perimeter straps may be used to hold such a pad in place, or the patch can be held in place directly with adhesive or just by the use of a very soft silicone with natural temporary adherence, such as a 0.1-2 mm thick transparent Durometer 5-10 hardness silicone gel pad. Many other bandage materials could be used that are reasonably translucent, since transparency is not necessarily a requirement, provided that suitable transmissivity is present. The size of this device can be any size required for the area to be treated. For PDT, these areas frequently are only a few square centimeters, but the treatment can sometimes cover a large part of the body. A separate adhesive may be utilized to hold the patch adhesive strip to the device. The perimeter material is an adhesive strip in this example, like a rectangular bandage, but many alternative shapes can exist. Small reservoirs or cavities can be built into the silicone that is placed against the skin interface and can be used to hold photosensitizer, lotion, local anesthetic, therapeutic agent(s), and/or other material(s) in place against the skin. These devices could potentially be cut to size by a physician, or an assortment of standard size patches could be provided in a kit. The patches could be pre-loaded with photosensitizers for ease of use and tighter dose control. These devices can be manufactured to be reused after cleaning, or they may be fabricated so as to be disposable. To stop the light exposure process, the patch could be covered with an opaque tape-like adhesive, or the intensity to the skin can be reduced using tape acting as a filter. Ultrasonic energy, heat, or vibration may also be applied through this device.

Figure 3:
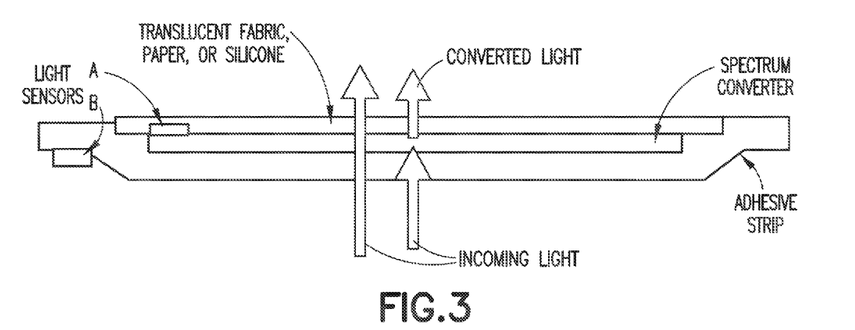
FIG. 3 is a cross-sectional elevation view of the spectrum converter of FIG. 2.

FIG. 3 is a cross-sectional elevation view of the PDT spectrum converter of FIG. 2, showing the details of the construction thereof.

Figure 4:
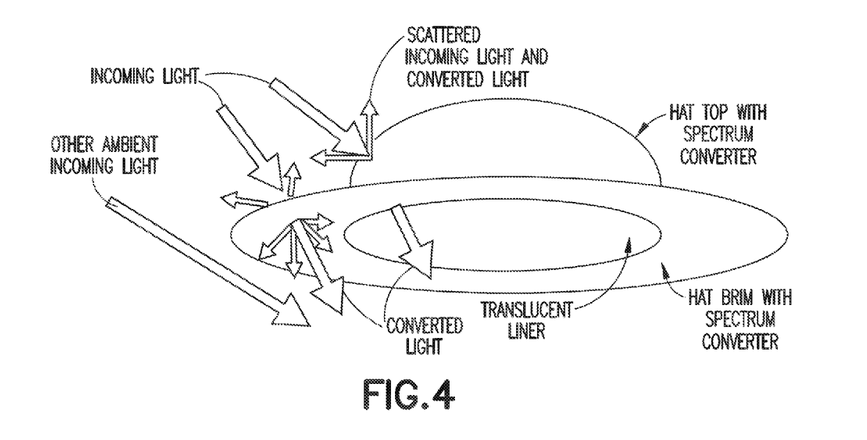
FIG. 4 is a schematic perspective view of a spectrum converter for ambient light according to a further embodiment of the disclosure, comprising a spectrum converter hat ("Embodiment 3").

FIG. 4 is a perspective schematic view of a spectrum converter for ambient light according to another embodiment of the disclosure, comprising a spectrum converter hat ("Embodiment 3"). As illustrated, the top head-engaging portion of the hat, as well as the brim of the hat, may incorporate a spectrum converter device in accordance with the present disclosure. The top portion of the hat may feature a liner, which may comprise a spectrum converter liner. The liner may be translucent. The hat therefore provides converted ambient light to the head and facial regions of the wearer. The spectrum converters in the hat may include dyes or phosphors that are optimized for a particular photosensitizer.

Figure 5:
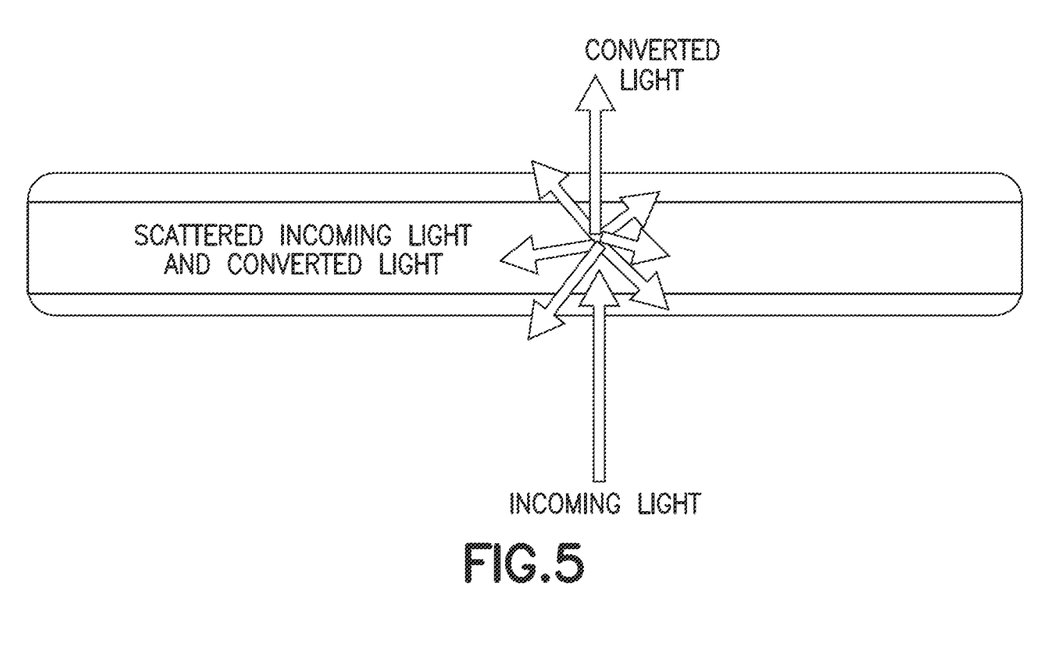
FIG. 5 is a cross-sectional view of a spectrum converter for ambient light according to another embodiment of the disclosure, comprising a spectrum converter fiber ("Embodiment 4").

FIG. 5 is a cross-sectional view of a spectrum converter for ambient light according to another embodiment of the disclosure, comprising a spectrum converter fiber ("Embodiment 4").

In Embodiment 4, the top layer of the device that rests against the skin may be a customized 1.35-1.45 refractive index <20 Durometer soft silicone gel (e.g., a NuSil™ gel) to enhance light transmission into the skin. Other suitable refractive index materials could also be used with, or instead of, silicone gel, but a non-liquid interface with index matching to the skin and an ability to minimize air pockets is highly preferred. Many aqueous solutions exist that can be adjusted to match a 1.4 index of refraction, e.g., sucrose:water solutions and glycerin:water solutions, which can be used if needed.

An optional UV blocking or converter dye layer can be provided around the fiber, with violet and/or blue-to-green emission. 410-430 nm perylene dyes may for example be employed for such purpose. The device may comprise a color converter matrix in a binder, or a coating on polymer or other translucent sheet. Organic dyes, e.g., 610 nm, 670 nm, 775 nm, and/or 820 nm perylene derivatives may be employed. The coating is optional, and TPP should be avoided in this embodiment to avoid skin irritation.

Figure 6:
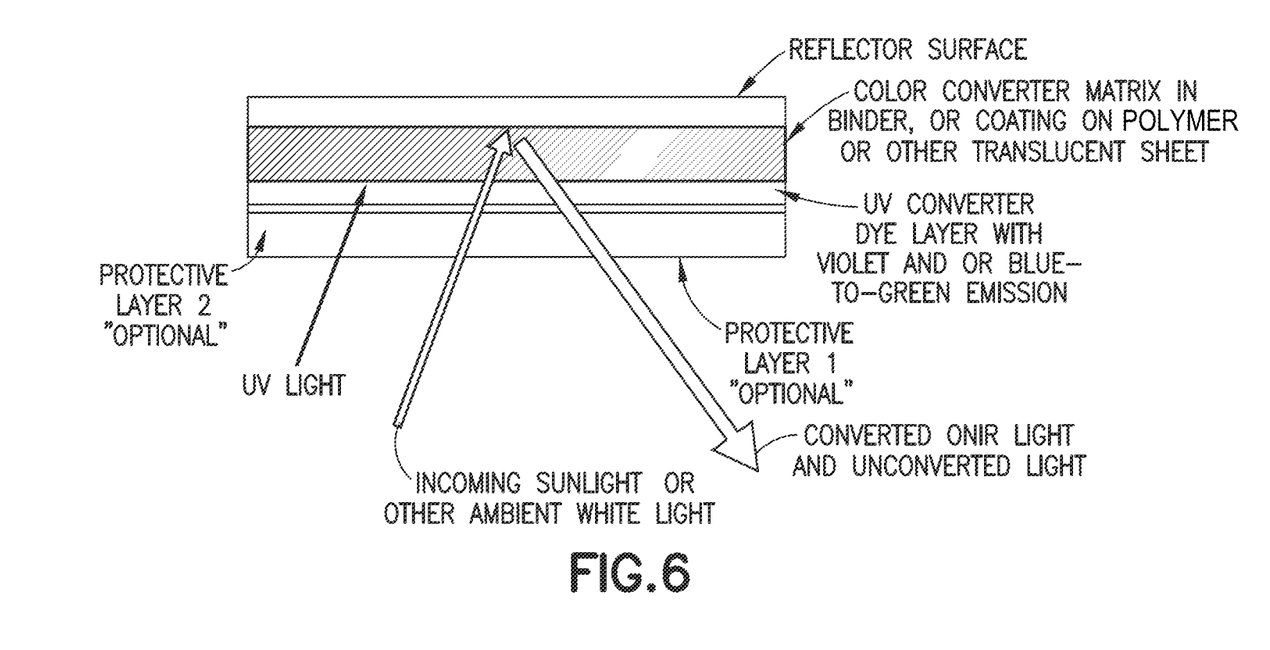
FIG. 6 is a schematic representation of a spectrum converter for ambient light according to one embodiment of the disclosure, comprising a reflective photoluminescent converter ("Embodiment 5").

FIG. 6 is a schematic representation of a spectrum converter for ambient light according to one embodiment of the disclosure, comprising a reflective photoluminescent converter ("Embodiment 5").

In the reflective photoluminescent converter of Embodiment 5, a UV converter dye layer with violet and/or blue-to-green emission is provided, which may for example comprise TPP or 410-430 nm perylene. The device may comprise a color converter matrix in a binder, or a coating on polymer or other translucent sheet. As one option, such layer may comprise phosphors or QDs, e.g., 650 nm oxynitride. As another option, such layer may comprise organic dye, e.g., 610 nm, 670 nm, 775 nm, and/or 820 nm perylene derivatives. An upper reflector surface layer is provided, which may comprise aluminum, silver, chromium, reflective mylar, etc.

An optional protective layer may be provided in the Embodiment 5 device, which may contain dye, phosphor, QDs, and/or other converters. An additional or alternative protective layer may likewise contain dye, phosphor, QDs, and/or other converters. For direct use on skin, such protective layer may comprise soft silicone, or predominantly translucent breathable material. This protective layer may comprise multiple sub-layers.

In one implementation of Embodiment 5, all layers of the device except for the converter layer (corresponding to layer 4 in the similar structure of Embodiment 1) comprise 1.4+/−0.05 index-matched silicone or other analogous material. In this configuration, the device only has significant refractive index mismatches into and out of the converter layer, and where light is first incident to the device.

Other specific embodiments are contemplated.

For example, an embodiment may be fabricated, in which the layer 4 of Embodiment 1 is replaced by index-matched silicone containing 650 nm or 670 nm phosphors. This embodiment provides a QY of 82% and exhibits a reduced number of reabsorptions, which have been minimized for the perylene ladder because of the unique way the absorption and emission curves of the dye series are partly mismatched to their nearest neighbors.

In other embodiments, to further improve light delivery into tissue, 1.4 refractive index silicon gels may be utilized as matrix materials for phosphor and/or quantum dot spectrum conversion materials to minimize light losses due to refractive index changes from the location at which light has entered the spectrum converter device until after light enters the skin. Alternative layers can comprise an index-matched liquid or gel interface to the skin or a body-shaped rigid material may be used, such as low index glass (e.g., low index glasses commercially available from Schott or Ohara) with indices of refraction at about ~1.35-1.45 at ~600-700 nm or ~650-850, depending on the specific glass that is selected.

In other embodiments, as in the device illustrated in FIG. 4, the device may be in the form of fibers. If the fibers can be coated, a simplified structure can be employed, comprising core fibers, e.g., of polyester, nylon, or acrylic, and only violet dye on the fiber coating, with no TTP or phosphors being used, and without any top and bottom optional layers. In still other embodiments, the fibers may be used without any coating on the fibers, with a dye, e.g., BASF Violet 570, being added directly to the core fiber with the other dyes.

Additional embodiments may be constituted in the manner of Embodiment 5 (FIG. 6), except for the adaptation for the mirror.

Other embodiments encompass light spectrum converting apparel, comprising or incorporating spectrum-converter materials absorbing sunlight or light from other ambient light sources, and reemitting light in predominantly the 600 nm-850 nm spectral range. Such apparel articles include, without limitation, hats, caps, visors, arm bands, leg bands, joint covers, footwear, shirts, trousers, shorts, dresses, swimsuits, coats, sweaters, sweatshirts, lingerie, underwear, gloves, and other apparel articles.

In various embodiments of the disclosure, thin flexible sheet- or web-form ambient light converter devices can be attached to backing materials such as fabric or mesh backings. The backing material in such embodiments can be suitably translucent, or it may comprise a very open weave woven web or fabric material.

The disclosure in other embodiments encompasses light spectrum-converting fibers for therapeutic or decorative apparel in which the spectrum converter material comprises a dye, phosphor, quantum dots, or photonic crystal array on translucent polymers, silicones, or as one or more coatings on polymer sheets, or other applicable materials. Scattering of light is permitted through sheets, pads, bands, body wraps, or bandage-like arrangements.

In additional embodiments, the disclosure provides for light spectrum converting apparel wherein the spectrum converter material is a dye, phosphor, quantum dots, or photonic crystal array on light reflective polymer sheets or as one or more coatings on polymer sheets or other translucent materials. Scattering of light is permitted.

Other embodiments of the present disclosure include light spectrum-converting apparel in which the spectrum converter material comprises a dye or phosphor in polymer fibers or as one or more coatings on synthetic or natural fibers. Applicable materials include, without limitation: (a) polyimides, polyesters, nylons, cotton, wool, and other fiber-based woven and non-woven fabrics; (b) porous membrane sheet materials (e.g., Gore-Tex® materials); (c) optical fibers or arrays of optical fibers; and (d) combinations of the foregoing.

Still other embodiments of the present disclosure comprise light spectrum-converting fabric in which the spectrum converter material comprises a dye or phosphor in polymer fibers or as one or more coatings on synthetic or natural fibers. Applicable materials include, without limitation: (a) polyimide or polyester fibers; and (b) fibers coated with aluminum or other reflector materials, including dichroic reflectors.

The ambient light source conversion devices and materials of the present disclosure enable the output light spectrum and/or source to be customized for specific applications, including, without limitation: (a) enhancement of therapeutic doses of light derived from sunlight or other primary light sources for activation of photosensitizers, wound healing, inflammation reduction, and/or realization of other light-activated benefits; (b) supply of energy for botanical plant, algae, and/or photo-bacteria growth; and (c) purification and antimicrobial treatment of water and/or other fluids, e.g., bodily fluids, with or without an added photosensitizer.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. A high quantum yield (QY) photoluminescent light spectrum conversion device for absorbing and converting sunlight or other available ambient light to a modified light spectrum output that contains 75% or more of its output radiant light spectrum in the over-580 nm red, near-infrared and/or infrared wavelength range, the device comprising two or more photoluminescent conversion materials that collectively absorb over 60% of normal angle ambient light that has entered the device in the 350 nm to 580 nm spectral range, and wherein the modified light spectrum output light emitted from within the device provides 75% or more of its output radiant light power in the 580 nm-850 nm spectral range, wherein the photoluminescent conversion materials are selected from the group consisting of dyes, phosphors, quantum dots, and photonic structures, wherein the device comprises one or more layers that are transmissive of at least 40% of normal angle ambient light in a spectral range of over 600 nm that has entered the device, and wherein the device does not utilize any electrical power supply for the production of the modified light spectrum output, the device further comprising an optical filter that is over 50% transmissive to normal angle ambient light in most of the red or near infrared spectral range that has entered the device, so that ambient red and near-IR light is added to the spectrum converted light and constitutes a portion of the output radiant light spectrum to the targeted surfaces.

2. The device of claim 1, wherein the photoluminescent conversion materials are coated on or overlie a mirror or non-specular reflective surface.

3. The device of claim 1, further comprising a monitoring assembly comprising at least one photosensor and configured to generate an output indicative of at least one of dose status, progress of light dosing, and completion of dosing, of the modified light spectrum output of the device.

4. The device of claim 1, further comprising a light control assembly that is configured to:
   (i) increase or decrease light passing though the device; (ii) deactivate the device, or otherwise reduce or block light coming from the device to the target surfaces when a predetermined light dose level of the modified light spectrum output of the device has been reached;
   (iii) modulate the intensity of the output modified light spectrum of the device in response to variable ambient light radiant intensity; and/or
   (iv) execute a light dose vs. time regimen for the modified light spectrum output of the device.

5. The device of claim 1, comprising a bandage structure incorporating the photoluminescent conversion materials and configured for application to the body of a subject for administration of the modified light spectrum output of the device, optionally further comprising an insert to be interposed between the body of the subject and the bandage structure, wherein the insert has an index of refraction matched to a surface of the body to be treated, and is adapted to therapeutically augment the administration of the modified light spectrum output of the device.

6. The device of claim 1, wherein the device is configured as a gel, cream, liquid, semisolid, or a state converting material.

7. The device of claim 1, further comprising at least one reflector arranged to reflect light to the photoluminescent conversion materials for enhanced conversion to the modified light spectrum output, and optionally further comprising at least one filter arranged to transmit reflected light in the spectral region of the modified light spectrum output, to said output.

8. The device of claim 1, wherein one or more of the photoluminescent conversion materials is spatially oriented to enhance the intensity of the modified light spectrum output.

9. The device of claim 1, wherein one or more of the photoluminescent conversion materials is comprised in an array of optical fibers.

10. The device of claim 1, wherein one or more of the photoluminescent conversion materials is comprised in one or more layers of applied coatings or laminate articles.

11. The device of claim 1, comprising fibers or fabric, comprising or coated with one or more of the photoluminescent conversion materials.

12. The device of claim 1, comprising a sheet, film, molded, moldable, or web article, comprising or coated with one or more of the photoluminescent conversion materials.

13. The device of claim 1, as disposed in light-supplying relationship to provide the modified light spectrum output to a light-utilizing system, wherein the light-utilizing system comprises a system selected from the group consisting of: botanical plant growth systems, algae growth systems, systems for the purification of water or body fluids, and systems for antimicrobial treatment of water or body fluids.

14. A high quantum yield (QY) photoluminescent light spectrum conversion device for absorbing and converting sunlight or other available ambient light to a modified light spectrum output that contains 75% or more of its output radiant light spectrum in the over-580 nm red, near-infrared and/or infrared wavelength range, the device comprising two or more photoluminescent conversion materials that collectively absorb over 60% of normal angle ambient light that has entered the device in the 350 nm to 580 nm spectral range, and wherein the modified light spectrum output light emitted from within the device provides 75% or more of its output radiant light power in the 580 nm-850 nm spectral range, wherein the photoluminescent conversion materials are selected from the group consisting of dyes, phosphors, quantum dots, and photonic structures, wherein the device comprises one or more layers that are transmissive of at least 40% of normal angle ambient light in a spectral range of over 600 nm that has entered the device, and wherein the device does not utilize any electrical power supply for the production of the modified light spectrum output, wherein the photoluminescent conversion materials comprise three or more of the following layers or mixtures or high efficiency photoluminescent materials including:
- a violet-UV absorber and violet-blue light emitter photoluminescent dye;
- a violet-blue absorber and blue-yellow light emitter photoluminescent dye;
- a green-yellow absorber and orange and/or red light emitter photoluminescent dye; and optionally
- a blue-green absorber and yellow-orange light emitter photoluminescent dye, and one or more absorbers with high light absorption in some portion of the under-580 nm spectral range matching a significant part of the emission spectrum of one or more or the above listed materials, that exhibit over 80% of their collective light emission over all of, and/or portions of the 580 nm to 950 nm spectral range.

15. The device of claim 14, wherein at least one of the photoluminescent dyes is substituted by or supplemented with material, selected from the group consisting of phosphors and quantum dots, that absorbs in the violet and/or blue, and emits predominantly in the red and/or near-IR spectral region, and wherein any of the various type photoluminescent layers or mixtures may be duplicated or repeated in multiple layers of the device.

16. A high quantum yield (QY) photoluminescent light spectrum conversion device for absorbing and converting sunlight or other available ambient light to a modified light spectrum output that contains 75% or more of its output radiant light spectrum in the over-580 nm red, near-infrared and/or infrared wavelength range, the device comprising two or more photoluminescent conversion materials that collectively absorb over 60% of normal angle ambient light that has entered the device in the 350 nm to 580 nm spectral range, and wherein the modified light spectrum output light emitted from within the device provides 75% or more of its output radiant light power in the 580 nm-850 nm spectral range, wherein the photoluminescent conversion materials are selected from the group consisting of dyes, phosphors, quantum dots, and photonic structures, wherein the device comprises one or more layers that are transmissive of at least 40% of normal angle ambient light in a spectral range of over 600 nm that has entered the device, and wherein the device does not utilize any electrical power supply for the production of the modified light spectrum output, further comprising a monitoring material that upon a predetermined exposure to ambient light or spectral region(s) thereof changes optical density and/or color to provide a visually discernible indication of status and/or completion of light dosage from the device.

17. A high quantum yield (QY) photoluminescent light spectrum conversion device for absorbing and converting sunlight or other available ambient light to a modified light spectrum output that contains 75% or more of its output radiant light spectrum in the over-580 nm red, near-infrared and/or infrared wavelength range, the device comprising two or more photoluminescent conversion materials that collectively absorb over 60% of normal angle ambient light that has entered the device in the 350 nm to 580 nm spectral range, and wherein the modified light spectrum output light emitted from within the device provides 75% or more of its output radiant light power in the 580 nm-850 nm spectral range, wherein the photoluminescent conversion materials are selected from the group consisting of dyes, phosphors, quantum dots, and photonic structures, wherein the device comprises one or more layers that are transmissive of at least 40% of normal angle ambient light in a spectral range of over 600 nm that has entered the device, and wherein the device does not utilize any electrical power supply for the production of the modified light spectrum output, further comprising a dose-limiting material that upon a predetermined exposure to ambient light or spectral region(s) thereof changes optical density to provide a predetermined light dosage of the modified light spectrum output of the device.

18. A method of light therapy treatment of a subject in need thereof, said method comprising generating a modified light spectrum output using a high quantum yield (QY) photoluminescent light spectrum conversion device for absorbing and converting sunlight or other available ambient light to a modified light spectrum output that contains 75% or more of its output radiant light spectrum in the over-580 nm red, near-infrared and/or infrared wavelength range, the device comprising two or more photoluminescent conversion materials that collectively absorb over 60% of normal angle ambient light that has entered the device in the 350 nm to 580 nm spectral range, and wherein the modified light spectrum output light emitted from within the device provides 75% or more of its output radiant light power in the 580 nm-850 nm spectral range, wherein the photoluminescent conversion materials are selected from the group consisting of dyes, phosphors, quantum dots, and photonic structures, wherein the device comprises one or more layers that are transmissive of at least 40% of normal angle ambient light in a spectral range of over 600 nm that has entered the device, and wherein the device does not utilize any electrical power supply for the production of the modified light spectrum output, the device further comprising an optical filter that is over 50% transmissive to normal angle ambient light in most of the red or near infrared spectral range that has entered the device, so that ambient red and near-IR light is added to the spectrum converted light and constitutes a portion of the output radiant light spectrum to the targeted surfaces, and exposing a body region of the subject to the modified light spectrum output.

19. The method of claim 18, wherein the light therapy treatment is carried out to treat:
- joints and muscles for reducing pain and inflammation;
- wounds for improving the rate of wound healing;
- acne, rosacea, skin tone, and other dermatological conditions, to improve healing, and reduce the population of bacteria or fungus that are directly or indirectly photosensitive to the light spectrum of the light therapy treatment;
- muscles for enhancing regeneration of tissue after exercise or other stress;
- hone areas to repair damage and improve bone density;
- head, neck, spine, or other body areas, for pain and inflammation, for mood treatments, for reducing damage from brain injuries, or for increasing generation of nerve stem cells;
- activation of photosensitizers in Or on the skin or tissue; or
- veterinary use on animals.

* * * * *